(12) United States Patent
Ouyang et al.

(10) Patent No.: US 11,446,409 B2
(45) Date of Patent: Sep. 20, 2022

(54) AGENT FOR BIOLOGICAL DAMAGE REPAIR OR HEMOSTASIS AND THE METHOD THEREOF

(71) Applicant: Haining Zhuluoji Biotechnology Co., Ltd., Haining (CN)

(72) Inventors: Hongwei Ouyang, Hangzhou (CN); Yi Hong, Hangzhou (CN); Feifei Zhou, Hangzhou (CN); Shufang Zhang, Hangzhou (CN)

(73) Assignee: HAINING ZHULUOJI BIOTECHNOLOGY CO., LTD., Haining (CN)

( * ) Notice: Subject to any disclaimer, the term of this patent is extended or adjusted under 35 U.S.C. 154(b) by 24 days.

(21) Appl. No.: 16/815,291

(22) Filed: Mar. 11, 2020

(65) Prior Publication Data

US 2020/0206383 A1 Jul. 2, 2020

Related U.S. Application Data

(63) Continuation-in-part of application No. PCT/CN2018/083882, filed on Apr. 20, 2018.

(30) Foreign Application Priority Data

Sep. 15, 2017 (CN) .......................... 201710833161.2

(51) Int. Cl.
| | | |
|---|---|---|
| *A61L 24/04* | (2006.01) | |
| *C07K 14/78* | (2006.01) | |
| *C08L 1/28* | (2006.01) | |
| *C08L 5/08* | (2006.01) | |
| *C08L 5/04* | (2006.01) | |
| *C07K 14/435* | (2006.01) | |

(52) U.S. Cl.
CPC ...... *A61L 24/043* (2013.01); *C07K 14/43518* (2013.01); *C07K 14/78* (2013.01); *C08L 1/286* (2013.01); *C08L 5/04* (2013.01); *C08L 5/08* (2013.01); *A61L 2430/02* (2013.01); *C08L 2312/00* (2013.01)

(58) Field of Classification Search
None
See application file for complete search history.

(56) References Cited

FOREIGN PATENT DOCUMENTS

| CN | 103822183 A | * | 5/2014 |
|---|---|---|---|
| CN | 105169465 A |   | 12/2015 |

(Continued)

OTHER PUBLICATIONS

English Language Translation of CN 103 822 183 A (2017). (Year: 2017).*

(Continued)

*Primary Examiner* — Dominic Lazaro
(74) *Attorney, Agent, or Firm* — NZ Carr Law Office

(57) ABSTRACT

The purpose of the present invention is to provide a light control agent and explore its application, and is expected to improve the tissue binding force and convenience of the existing biological glue material by providing a new reagent or material for biological damage or homeostasis. In one of embodiment, this invention provides an agent for repairing biological damage or homeostasis, wherein the agent comprises a natural biological macromolecule modified by the photo-responsive cross-linking group.

13 Claims, 4 Drawing Sheets

No forming glue forming glue

(56) References Cited

FOREIGN PATENT DOCUMENTS

| CN | 106822183 A | 6/2017 |
| CN | 108187130 A | 6/2018 |
| WO | WO 2015138187 A1 | 9/2015 |
| WO | WO 2017139318 A1 | 8/2017 |

OTHER PUBLICATIONS

PCT/CN2018/083882 International Search Report and Written Opinion dated Jul. 23, 2018, 6 pp.

\* cited by examiner

No forming glue                    forming glue

FIG. 5
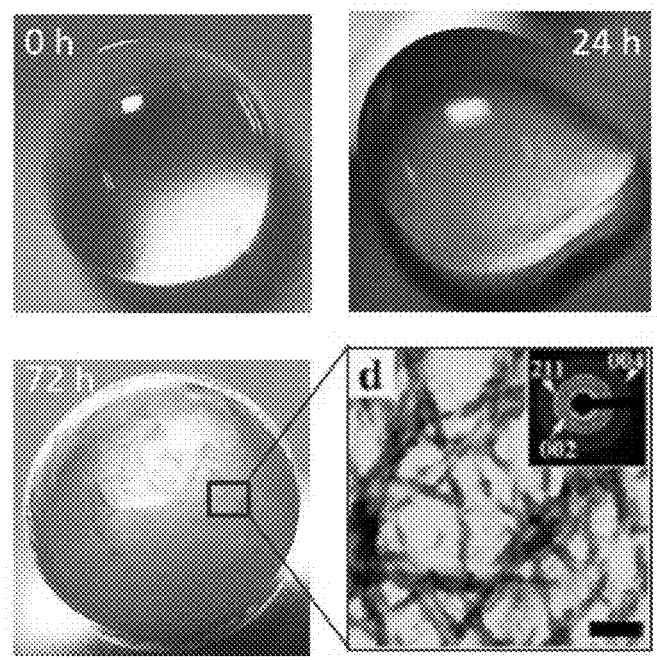
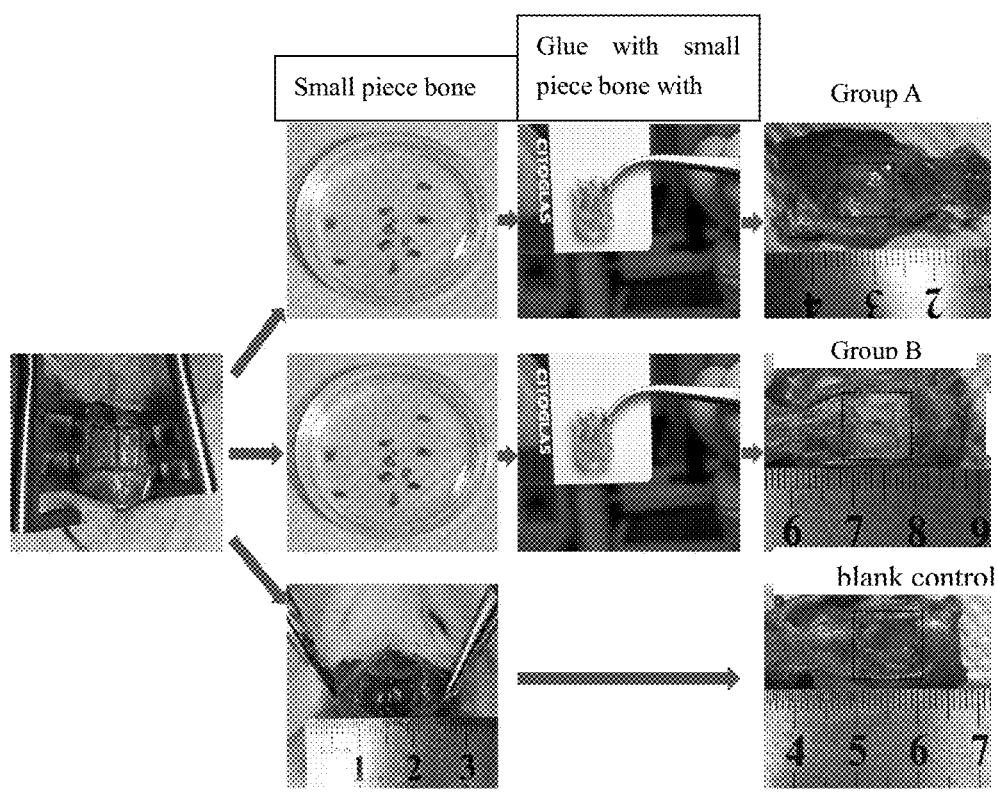
FIG. 6A
FIG. 6B
FIG. 6C

AGENT FOR BIOLOGICAL DAMAGE REPAIR OR HEMOSTASIS AND THE METHOD THEREOF

CROSS REFERENCE TO RELATED APPLICATION

This application is a continuation-in-part to International Patent Application No. PCT/CN2018/083882, filed Apr. 20, 2018, which claims the priority benefit of Chinese Patent Application No. 201710833161.2, filed Sep. 15, 2017. Each of these applications is incorporated by reference herein in its entirety.

FIELD OF THE INVENTION

The present invention relates to a light-control bio-glue and its application, and more particularly it relates to a reagent which capable of performing a biological tissue repair or hemostasis and the use of this reagent. The present invention also relates a bone-adhesive bioglue for accelerating fracture healing and an application thereof.

BACKGROUND OF THE INVENTION

The background art below will help to understand this invention, and it cannot be deemed as the prior art.

Hemostasis and suture are the most important technique used in clinical medicine, which is directly related to the patient's life and safety. Quick hemostasis and wound suture can effectively reduce the casualty's death rate. However, there is no quicker and more convenient method for hemostasis and suture in cases like intestinal wall bleeding, disseminated bleeding of viscera and liver resection.

At present, the major hemostatic materials at home and abroad include fibrin glue, gelatin, collagen, and oxidized cellulose, chitosan and calcium alginate. These products mostly appear in the form of spongy, fibrous, powdery and membranous. Although these products can meet the needs of general traumatic hemostasis, in clinical trauma, the form and shape of wounds is complex, and these products have poor plasticity that cannot fully meet the needs of different types of wounds and bleeding in patients.

In recent years, hydrogels have attracted a great deal of attention from researchers because of their convenient operation, strong plasticity and the ability to maintain the moist external environment of wounds. Rutledge G Ellis-Behnke et al. utilized a self-assembled fibrin gel as a hemostatic gel that can promote platelet coagulation and rapidly coagulate blood within 15 seconds (R. G Ellis-Behnke, Y-X. Liang, D. K. C. Tay, P. W. F. Kau, G E. Schneider, S. Zhang, W. Wu, K.-F.). So, Nano hemostat solution: immediate hemostasis at the nanoscale, Nanomedicine: Nanotechnology, Biology and Medicine, 2 (2006) 207-215). Japanese scholars Qingshui Qingyan et al. disclosed a collagen hydrogel, which was prepared by mixing thoroughly collagen and a certain proportion of polyglutamic acid, and then adding a certain volume of water-based aqueous solution of carbodiimide with incubating for 5-120 seconds. This collagen hydrogel has the characteristics of fast gelling speed, good binding force and good biocompatibility, etc (Qingshui Qingyan, collagen hydrogel, Patent Application Number 98805532.5). Keumyeon Kim et al used hydroxy-modified polyethylene glycol and tannin to form a TAPE-OH gel that is capable of forming strong adhesions with tissue through hydrogen bonding and can stop bleeding within 30 seconds (K. Kim, M. Shin, M.-Y. Koh, J. H. Ryu, M. S. Lee, S. Hong, H. Lee, TAPE: A Medical Adhesive Inspired by a Ubiquitous Compound in Plants, Adv. Funct. Mater., 25 (2015) 2402-2410). Linyong Zhu et al. mixed hyaluronic acid which was modified by N-(2-aminoethyl)-4-(4-(hydroxymethyl)-2-methoxy-5-nitrophenoxy) butyrylamide with chitosan to form a Non-free-radical photochemical crosslinked hydrogel. This hydrogel had tissue adhesion and was effective on skin repair and wound closure (Yang Y, Zhang J, Liu Z, et al. Tissue— Integratable and Biocompatible Photogelation by the Imine Crosslinking Reaction. Advanced Materials, 2016) (Preparation of Non-free-radical photochemical crosslinked hydrogel, the product and it applications. Patent Application Number 201410698239.0).

However, the gels mentioned above are not fast enough to stop the bleeding, the mechanical strength and their binding force with tissues are not enough, and they are difficult to control bleeding rapidly in the case of heavy bleeding. Therefore, it is necessary to find an improved material to overcome some of the deficiencies of the traditional techniques.

Fracture is a common disease that is directly related to patients' life and even their safety. At present, the treatment for fractures is mainly to restore the bone structure through the implantation of steel plates, screws, and other means for fixing the bone, thereby promoting the body to self-regenerate and repair. However, the above-mentioned internal fixation method usually requires surgery to take out the fixation appliance, which can cause secondary damage to the body. Besides, for some comminuted fractures, bone defects often occur after the fixation of the plate and other fixation methods, and those bone fragments cannot be well reset. If forced to reset, it will cause excessive peeling to cause dead bones, resulting in postoperative bone block absorption, poor fracture healing, delayed healing, and even non-healing, which requires second surgery for treatment. In this case, bone graft treatments, including autologous bone grafts and allogeneic bone grafts, are often used clinically. Generally, the autogenous bone is often taken from the ilium. In the process of taking a part of the ilium, it is easy to damage the peripheral nerves and blood vessels, causing damage to the body and adverse reaction, for example, pain at the bone removal site. The implantation of allogeneic bone will cause a certain degree of rejection in the body, the bone formation ability of allogeneic bone is poor, and the formation of bone tissue is little, which may lead to the failure of transplantation treatment.

What's more, the above-mentioned several treatment methods for fractures are to treat fractures by self-regeneration and repair of the body. The regeneration speed is slow and most of them require multiple operations which are relatively complicated.

SUMMARY OF THE INVENTION

The purpose of the present invention is to provide a light control agent and explore its application, and is expected to improve the tissue binding force and convenience of the existing biological glue material by providing a new reagent or material for biological damage or hemostasis.

In one aspect, the present invention provides an agent for biological damage or hemostasis, the agent contains natural biological macromolecules modified by light-responsive crosslinking groups. In some preferred modes, the reagent includes other necessary components. Preferably, the other necessary components include natural biological macromolecules modified with o-nitrobenzyl type photo trigger. Preferably, the reagent may further contain a photo initiator and/or deionized water.

In some preferred embodiments, the final mass concentration of the natural biological macromolecule modified by the light-responsive cross-linking group and/or the natural biological macromolecule modified by o-nitrobenzyl light trigger are 0.1~20% which are based on the mass of the deionized water.

Preferably, the final concentration of the photo initiator is 0.001 to 10% based on the mass of the deionized water.

Preferably, the photo-reactive crosslinking group in the photo-responsive crosslinking group modified natural biological macromolecule has a graft substitution rate of 5-90%.

Preferably, the light-responsive crosslinking group is methacrylamide or methacrylic anhydride, one of methyl maleic anhydride, or their mixture.

Preferably, the o-nitrobenzyl type photo initiator in the o-nitrobenzyl type photo initiator-modified natural biological macromolecule has a graft substitution rate of 1-100%.

In some preferred embodiments, the natural biological macromolecule modified by ortho-nitrobenzyl class photo initiator is represented as the formula (I), in the formula (I), R1 is —H or is selected in ester bonds from —CO(CH2)$_x$CH3, —CO(CH2CH2O)$_x$CH3, CO(CH2)$_x$(CH2CH2O)$_y$CH3, or is selected in ether bonds from —(CH$_2$)$_x$CH$_3$, —(CH$_2$CH$_2$O)$_x$CH$_3$, —(CH$_2$)$_x$(CH$_2$CH$_2$O)$_y$CH$_3$、

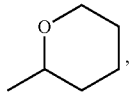

or is selected in Carbonate bonds from —COO(CH$_2$)$_x$CH$_3$, —COO(CH$_2$CH$_2$O)$_x$CH$_3$, —COO(CH$_2$)$_x$(CH$_2$CH$_2$O)$_y$CH$_3$, or is selected in isocyanate bonds from —CONH(CH$_2$)$_x$CH$_3$、—CONH(CH$_2$CH$_2$O)$_x$CH$_3$、—CONH(CH$_2$)$_x$(CH$_2$CH$_2$O)$_y$CH$_3$, Wherein, x and y≥0 and are integers; or R2 is —H or a substituent selected from the group consisting of —O(CH2)$_x$CH3, —O(CH2CH2O)$_x$CH3, —O(CH2)$_x$(CH2CH2O)$_y$ CH3, where x And y≥0 and is an integer; or R3 is selected from the group consisting of an amino type linkage —O(CH2)xCONH (CH2)yNH—, a halogenated type linkage —O(CH2) x- and a carboxyl type linkage —O)xCO—, where x and y≥1 and are integers; or R4 is —H or —CONH(CH2)$_x$CH3 where x≥0 and is an integer; P1 is a biological macromolecule;

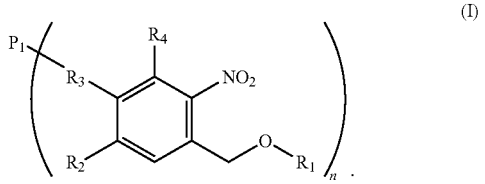

(I)

Further, it is preferable that the o-nitrobenzyl type photo trigger is o-nitrobenzyl.

Further, the natural biological macromolecules modified by the photo-responsive cross-linking group and/or modified by o-nitrobenzyl light trigger are hyaluronic acid, gelatin, sodium alginate, Chondroitin sulfate, silk fibroin, chitosan, carboxymethylcellulose or collagen, or a mixture comprised by several kinds of these substances mentioned above.

Further, the photo initiator is 2-hydroxy-4 (2-hydroxyethoxy)-2-methylpropiophenone (12959) or lithium phenyl-2,4,6-trimethylbenzoylphosphinate (LAP).

Preferably, the mass ratio of the photo initiator and the natural biological macromolecule modified by the photo-responsive crosslinking group is 1~3:100.

Further, the Light-reactive crosslinking group-modified natural biological macromolecule has a graft substitution rate of 10-30%. The o-nitrobenzyl type photo initiator modified natural biological macromolecule has a graft substitution rate of 1~20%.

Further, the natural biological macromolecule modified by light-responsive crosslinking group-is methacrylic acid anhydride-modified gelatin with a graft substitution rate of 10%; or methacrylamide-modified gelatin with a graft substitution rate of 90%; or methacrylic anhydride modified gelatin with a graft substitution rate of 40%; or methacrylamide modified gelatin with a graft substitution rate of 20%; or methacrylic anhydride modified collagen with a graft substitution rate of 30%; or methacrylic anhydride modified chondroitin sulfate with a graft substitution rate of 90% or methacrylamide-modified carboxymethyl cellulose with a graft substitution rate of 10%, or a mixture comprised by several kinds of these substances mentioned above.

Further, the natural biological macromolecule modified by the o-nitrobenzyl light trigger is o-nitrobenzyl modified hyaluronic acid with a graft substitution rate of 100%; or o-nitrobenzyl modified Sodium Alginate with a graft substitution rate of 50%; or o-nitrobenzyl modified chondroitin sulfate with a graft substitution rate of 10%; or o-nitrobenzyl modified gelatin with a graft substitution rate of 30%; or O-nitrobenzyl modified silk fibroin with a graft substitution rate of 90%; or o-nitrobenzyl modified collagen with a graft substitution rate of 100% or o-nitrobenzyl modified chitosan with a graft substitution rate of 10%, or a mixture comprised by several kinds of these substances mentioned above.

Further, the final mass concentration of the natural biological macromolecule modified by the photo responsive crosslinking group is 3-10% based on the mass of deionized water, and the final mass concentration of the natural biomolecule modified by the o-nitrobenzyl light trigger is 2-4% based on the mass of deionized water, and the final concentration of photo initiator is 0.03-0.2% based on the mass of deionized water.

In another aspect, the invention provides the application f the photo responsive crosslinkable group-modified natural biomacromolecule in the preparation of a tissue repair or hemostatic agent. In some preferred embodiments, the reagent also includes o-nitrobenzyl light-modified natural biological macromolecules. Preferably, the reagent also includes a photo initiator and/or deionized water. The preferred final mass concentration of the photo initiator is 0.001 to 1% based on the mass of deionized water.

In some preferred embodiments, the final mass concentration of natural biological macromolecules modified by photo-responsive cross-linking groups modified natural biomolecules and o-nitrobenzyl light-trigger modified natural biomolecules is both 0.1 to 10% based on the mass of deionized water.

The graft substitution rate of the light-responsive cross-linking group in the photo-responsive crosslinking group-modified natural biomacromolecule is preferably 10 to 90%. Preferably, the photo responsive crosslinking group is methacrylamide or methacrylic anhydride.

Preferably, the graft substitution rate of the o-nitrobenzyl group light trigger in the natural biological macromolecule modified by the o-nitrobenzyl type light trigger is 1 to 100%.

In another aspect, the present invention also provides an application of the light-controlled biological glue in preparing a hemostatic agent.

The present invention also provides an application of the light-controlled biological glue in preparing a tissue repair agent.

Further, the application is as follows: the light-controlled biological glue is injected into a bleeding wound or tissue site which need to be repaired, and then irradiating it for 1 to 10 s by the light with a wavelength range of 350-450 nm and an energy density of 20-150 mW/cm$^2$. After that the biological glue can be cured by cross-linking, so as to quickly control bleeding or repair tissue.

In another aspect, the invention also provides a method of repairing biological tissue or hemostasis, the method comprising: providing an agent comprising a photo responsive crosslinked group modified natural biological macromolecule, The agent is applied to the biological tissue or the bleeding site of tissues.

The method includes injecting the light-controlled biological glue into a bleeding wound or tissue site that needs to be repaired.

In some preferred embodiments, the method includes: irradiating with light having a wavelength range of 350-450 nm and an energy density of 20-150 mW/cm$^2$. Preferably, the irradiation time is 1 to 10 s, and the biological glue can be cross-linked and solidified thus can be used to control bleed rapidly or repair the tissues.

In some preferred embodiments, the reagent also includes o-nitrobenzyl phototrigger-modified natural biological macromolecules. Preferably, the reagent also includes a photo initiator and/or deionized water. The preferred final mass concentration of the photo initiator is 0.001 to 1% based on the mass of deionized water.

In some preferred embodiments, the final mass concentration of the natural biological macromolecules modified by photo-responsive cross-linking groups and the o-nitrobenzyl light-trigger modified natural biomolecules are 0.1 to 10% which are based on the mass of the deionized water.

The graft substitution rate of the light-responsive crosslinking group in the photo-responsive crosslinking group-modified natural biomacromolecule is preferably 10 to 90%. Preferably, the photo responsive crosslinking group is methacrylamide or methacrylic anhydride.

Preferably, the graft substitution rate of the o-nitrobenzyl group light trigger in the natural biological macromolecule modified by the o-nitrobenzyl type light trigger is 1 to 100%.

We found that the natural biological macromolecules modified by light-responsive cross-linking groups can rapidly enhance wound healing and repair, as well as have a rapid hemostatic function. In particular, the use of natural biomacromolecules modified by o-nitrobenzyl light-trigger can significantly enhance the application effect.

It was speculated that the effects of natural biomacromolecules modified by light-responsive cross-linking groups are mainly displayed as the following two aspects: 1. The self-crosslinking reaction of the photo responsive cross-linking groups to rapidly form into gel state after light irradiation; 2. increasing the mechanical strength of the gel by providing amino groups to react with aldehyde groups, which generated from light-triggering o-nitrobenzyl groups modified natural biological macromolecules after light irradiation. Practically, the mainly roles of light triggering o-nitrobenzyl groups modified natural biological macromolecules including: 1. proving aldehyde groups after light irradiation to react with the amino groups on the surface of wound tissue, and thus making the gel produce strong tissue adhesion; 2. proving aldehyde groups after light irradiation to react with the amino groups on the natural biological macromolecules modified by photo-responsive crosslinking groups, and increasing the mechanical strength of the gel.

The invention utilizes the light triggering o-nitrobenzyl groups modified natural biological macromolecules to generate aldehyde group after light excitation, which chemically reacts with the amino group in the wound tissue to form a strong chemical bond, and then strongly bind to the surface of the wound tissue. Simultaneously, the light triggering o-nitrobenzyl groups modified natural biological macromolecules can rapidly solidify and seal the wound under light irradiation, and thus achieving the purpose of rapid hemostasis and wound repair. The light triggering o-nitrobenzyl groups modified natural biological macromolecules in the present invention is an ideal fast hemostatic biological glue material that can be used to replace some wound suture agents.

In fourth aspect, the present invention is to provide a bone-adhesive bioglue for accelerating fracture healing and the application thereof. The bone-adhesive bioglue directly binds fracture fragments and fractures, thereby solving the problems, such as slow healing speed and inconvenient operation, of the existing fracture treatment methods.

The present invention provides a method of bone adhesion for accelerating fracture healing. The method comprises providing a bioglue, applying the bioglue to a fracture lesion site, and irradiating the fracture lesion site coated by the bioglue with light of a certain wavelength and energy.

In some preferred embodiments, the bioglue comprises photo-responsive crosslinking group modified natural biomacromolecules; o-nitrobenzyl-based light trigger modified natural biomacromolecules, photo initiators, and osteogenic nanoparticles.

The present invention provides a bone adhesion bioglue for accelerating fracture healing. The bioglue comprises photo-responsive crosslinking group modified natural biomacromolecules; o-nitrobenzyl-based light trigger modified natural biomacromolecules, photo initiators, and osteogenic nanoparticles.

In some preferred embodiments, the bioglue comprises deionized water.

In some preferred embodiments, the final mass concentration of the photo-responsive crosslinking group-modified natural biomacromolecules and/or the o-nitrobenzyl-based light trigger-modified natural biomacromolecules is 0.1% to 10% by the mass of the deionized water.

In some preferred embodiments, the final mass concentration of the photo initiators in the bioglue is 0.001% to 1% by the mass of the deionized water.

In some preferred embodiments, the final mass concentration of the osteogenic nanoparticles in the bioglue is 0.001% to 10% by the mass of the deionized water.

In some preferred embodiments, the photo-responsive crosslinking group-modified natural biomacromolecule in the bioglue has a graft-replacement ratio of 10% to 90% by the photo-responsive crosslinking group.

In some preferred embodiments, the photo-responsive crosslinking group is methacrylamide or methacrylic anhydride.

In some preferred embodiments, the o-nitrobenzyl-based light trigger-modified natural biomacromolecule in the bioglue has a graft-replacement ratio of 1% to 100% by the o-nitrobenzyl-based light trigger.

Further, the o-nitrobenzyl light trigger modified natural biomacromolecule is represented by the formula (I). In the formula (I), R1 is —H or is an ester bond selected from —CO(CH$_2$)$_x$CH$_3$, —CO(CH$_2$CH$_2$O)$_x$CH$_3$, and —CO(CH$_2$)$_x$(CH$_2$CH$_2$O)$_y$CH$_3$, an ether bond selected from —(CH$_2$)xCH3, —(CH2CH2O)xCH3, —(CH2)x(CH2CH2O)yCH3, a carbonate linkage selected from —COO(CH2)xCH3, —COO(CH2CH2O)xCH3, —COO(CH2)x(CH2CH2O)yCH3, an isocyanate bond selected from —CONH(CH2)xCH3, —CONH(CH2CH2O)xCH3, —CONH(CH2)x(CH2CH2O)yCH3, wherein x and y 0 and are integers; R2 is —H or is a substituent selected from —O(CH2)xCH3, —O(CH2CH2O)xCH3, —O(CH2)x of (CH2CH2O)yCH3, wherein x and y≥0 and are integers; R3 is selected from the group consisting of an amino-type linkage —O(CH2)xCONH(CH2)yNH—, a halogenated linkage-O(CH2)x- and a carboxy-type linkage —O(CH2)xCO—, wherein x and y≥1 and are integers; R4 is —H or —CONH(CH2)xCH3, wherein x≥0 and is an integer; P1 is a biomacromolecule:

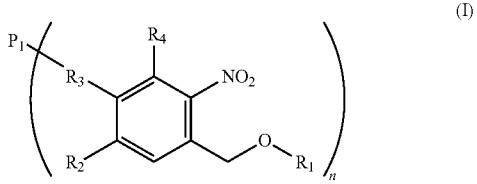

Further, preferably, the o-nitrobenzyl-based light trigger is o-nitrobenzyl.

Further, the natural biomacromolecule modified by the photo-responsive crosslinking group or the o-nitrobenzyl-based phototrigger is one of the following biomacromolecules, hyaluronic acid, gelatin, sodium alginate, chondroitin sulfate, silk fibroin, chitosan, carboxymethyl cellulose or collagen.

Further, the photo initiator in the bioglue is 2-Hydroxy-4'-(2-hydroxyethoxy)-2-methylpropiophenone or lithium phenyl-2,4,6-trimethylbenzoylphosphinate (LAP). In the bioglue, the mass ratio of the photo initiators and the natural biomacromolecules modified by the photo-responsive crosslinking group is from 1 to 3:100.

In some preferred embodiments, in the bio-glue, the osteogenic nanoparticle is NanoACP, NanoTCP or NanoHAP.

In some preferred embodiments, the osteogenic nanoparticle has a particle size of 1 to 50 nm.

In some preferred embodiments, the photo-responsive crosslinking group-modified natural biomacromolecule in the bioglue has a graft-replacement ratio of 10% to 30% by the photo-responsive crosslinking group; the o-nitrobenzyl-based light trigger-modified natural biomacromolecule in the bioglue has a graft-replacement ratio of 1% to 20% by the o-nitrobenzyl-based light trigger.

Further, the natural biomacromolecule modified by the photo-responsive crosslinking group is a gelatin, modified by methacrylic anhydride, having a graft substitution ratio of 10%, a gelatin, modified by methacrylamide, having a graft substitution ratio of 90%, a gelatin, modified by methacrylic anhydride, having a graft substitution ratio of 40%, a gelatin, modified by methacrylamide, having a graft substitution ratio of 20% gelatin, a collagen, modified by methacrylic anhydride, having a graft substitution ratio of 30%, a chondroitin sulfate, modified by methacrylic anhydride, having a graft substitution ratio of 90% or a carboxymethylcellulose, modified by methacrylamide, having a graft substitution ratio of 10%.

Further, the natural biomacromolecule modified by the o-nitrobenzyl light trigger is an o-nitrobenzyl base-modified hyaluronic acid having a graft substitution ratio of 100%, a o-nitrobenzyl base-modified sodium alginate having a graft substitution ratio of 50%, a o-nitrobenzyl base-modified chondroitin having a graft substitution rate of 10%, a o-nitrobenzyl base-modified gelatin having a graft substitution rate of 30%, a o-nitrobenzyl base-modified silk fibroin having a graft substitution rate of 90%, a o-nitrobenzyl base-modified collagen having a graft substitution rate of 100% or a o-nitrobenzyl base-modified chitosan having a graft substitution rate of 10%.

Further, the final mass concentration of the photo-responsive crosslinking group-modified natural biomacromolecules is 3% to 10% by the mass of deionized water. The final mass concentration of the o-nitrobenzyl-based light trigger-modified natural biomacromolecules is 2% to 4% by the mass of deionized water. The final mass concentration of photo initiators in the bioglue is 0.03% to 0.2% by the mass of deionized water.

The invention also provides an application of the bone-adhesive bioglue which is described above, accelerating fracture healing in fracture surgery.

The invention utilizes an -based light trigger to generate an aldehyde group after light excitation, and the generated aldehyde group and amino group can react to form a strong chemical bond. Under this mechanism, the natural biomacromolecule modified by the o-nitrobenzyl-based light trigger and the tissue surrounding the bone are combined (the main reason for the tissue adhesion is that the o-nitrobenzyl-based light trigger generates an aldehyde group after light irradiation, and then chemically bonds with the amino group in the tissue), and strongly bind to the bone tissue. The photo-responsive crosslinking group-modified natural biomacromolecules rapidly solidify under illumination to achieve the purpose that rapidly bonding the bone fragments to the surrounding bone tissue; after binding the bone fragments to the bone tissue, the osteogenic nanoparticles enter the natural biomacromolecules modified by photo-responsive crosslinking group, and then the osteogenic nanoparticles are enriched and mineralized, which accelerates new bone formation and fracture healing. It is an ideal bone-adhesive bioglue material for rapid repair of fractures.

BENEFITS

The bio-viscosity of the light-controlled biological glue can be controlled by light activation in the present invention. Prior to photoexcitation, the biological glue does not contain aldehyde groups to react with the amino groups on the wound tissue. Thus, it is not bioadhesive in this state. After photoexcitation, the aldehyde groups are generated on light triggering o-nitrobenzyl groups modified natural biological macromolecules, which can react with the amino group on the wound tissue quickly, so that the biological glue has good bio-viscosity. Moreover, the tissue adhesive capacity of the biological glue can be enhanced by increasing the concentration of light triggering o-nitrobenzyl groups modified natural biological macromolecules.

In the present invention, two kinds of natural biological macromolecules, which modified by light-responsive crosslinking groups and light triggering o-nitrobenzyl groups, respectively to form a biological glue for hemostasis and tissue repair in the medical fields. Importantly, this biological glue has good biosafety and high applicability, and it also can be gelatinized within 1 to 30 s, to achieve rapid hemostasis and wound tissue repair.

The bioadhesiveness of the bone-adhesive bioglue that accelerates fracture healing of the present invention can be controlled by illumination activation. Before the illumination activation, the bioglue do not contain an aldehyde group and could not react with the amino groups on the tissue, so there is no tissue stickiness. After the activation of the illumination, the aldehyde group is generated on the o-nitrobenzyl-based light trigger molecule, which can rapidly react with the amino group on the tissue, so that the bioglue can have good bioadhesiveness.

The osteogenic nanoparticles can enter the molecular interstitial pore of the photo-responsive crosslinking group-modified natural biomacromolecules and they are enriched and mineralized to accelerate new bone formation. The viscosity of the bioglue can be increased by increasing the concentration of the natural biomacromolecules modified by the o-nitrobenzyl-based light trigger. The invention adopts natural biomacromolecules modified by photo-responsive crosslinking groups, natural biomacromolecules modified by o-nitrobenzyl-based light triggers and osteogenesis nanoparticles, all of which have good biosafety and can be easily used for medical bone tissue adhesion and repair. It can be glued in 1-30 seconds to achieve rapid bone repair and accelerate fracture healing.

BRIEF DESCRIPTION OF THE DRAWINGS

FIG. 2A: removing some part of the liver lobe; FIG. 2B: bleeding; FIG. 2C: coating with biological glue; FIG. 2D: illumination;

FIG. 2E: immediately stopping bleeding after illumination; FIG. 2F: no bleeding was observed after 30 minutes.

FIG. 3A: isolation of femoral artery; FIG. 3B: clamping at both ends with vascular forceps, and a 1 mm orifice is opened on the femoral artery with a scalpel; FIG. 3C: blood spurting out from the wound after loosening the proximal forcep; FIG. 3D: coating the wound with biological glue, FIG. 3E: illumination; FIG. 3F: no bleeding after releasing the proximal forcep; FIG. 3G: cutting off the artery between the gap and the distal end, FIG. 3H: blood spurting again after cutting off, indicating the blood vessel is unobstructed.

FIG. 4A: making a 3 mm wound in the intestine; FIG. 4B: injecting iodophor at upstream of the intestine and the iodophor leaks out from the wound, FIG. 4C: covering the gap with biological glue; FIG. 4D: illumination; FIG. 4E: injecting iodophor at upstream of the intestine after illumination and no iodophor leaks out, while the downstream of intestinal is significantly bulged, FIG. 4F: iodophor is leaking out from downstream of intestine, indicating that the wound was well sealed and the intestinal tract is unobstructed.

FIG. 5 shows the mineralization process if the osteogenic nanoparticles after the bioglue is glued (embodiment 1) and it illustrates mineralization results at different time points after illumination treatment.

FIGS. 6A-6C are photographs showing the repairing process of the rat skull comminuted fracture via using the present invention.

Light-Responsive Cross-Linking Group-Modified Natural Biomacromolecules

Figure 1:
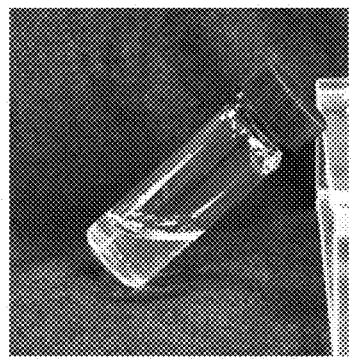
FIG. 1 is a photograph showing the before (left) and after (right) gelatinization of light-control biological glue, which produced according to the method described in the first embodiment of the present invention.
Figure 1:
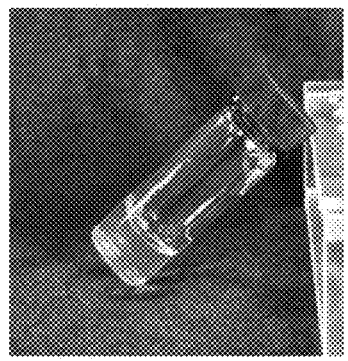

The present invention team surprisingly found that the natural biological macromolecules modified by light-responsive cross-linking groups could be used to repair damaged tissues or hemostasis. The general role of the substance may be wound closure. The so-called wound closure is just means seal the wound, just like the role of a patch, but cannot promote wound healing or stanch bleeding. However, the new role and function of the natural biological macromolecules modified by light-responsive cross-linking groups was unexpectedly found in the present invention.

In some specific embodiments, the light-responsive cross-linking group refers to methacrylamide, methacrylic anhydride or methyl maleic anhydride, or a mixture of them. Alternatively, the groups listed in the following literature: Colosi C, Shin S R, Manoharan V, et al. Microfluidic Bioprinting of Heterogeneous 3D Tissue Constructs Using Low-Viscosity Bioink Advanced Materials, 2016, 28 (4): 677-684) or some other groups capable of light responsiveness can be used in the present invention.

In some specific embodiments, the light-responsive cross-linking groups are capable of crosslinking with native macromolecules. Further, the light-responsive cross-linking group-modified natural biological macromolecule could be one of hyaluronic acid, gelatin, sodium alginate, chondroitin sulfate, silk fibroin, chitosan, carboxymethylcellulose or collagen, or a mixture of comprised by several kinds of them, or other known or unknown macromolecular substances in future, or synthetic molecules. Natural macromolecules are only a preferred solution, and these natural macromolecules can also be formed by artificial modification, or reprocessing, and will not be elaborated here.

Further, the photo-reactive cross-linking group-modified natural biological macromolecule has a graft substitution rate of 1% to 100%. It can be 1%, 2%, 3%, 5%, 10%, 15%, 20%, 25%, 30%, 35%, 40%, 45%, 50%, 60%, 70%, 80%, 90%, 100%, or a range between any two of the above values.

Further, the photo-reactive crosslinked group-modified natural biological macromolecule can be one of the compound or a mixture of several compounds listed as follows: methacrylic anhydride-modified gelatin with a graft substitution rate of 10%; methacrylamide-modified gelatin with a graft substitution rate of 90%; methacrylic anhydride-modified gelatin with a graft substitution rate of 40%; methacrylamide-modified gelatin with a graft substitution rate of 20%; methacrylic anhydride modified collagen with a graft substitution rate of 30%; methacrylic anhydride-modified chondroitin sulfate with a graft substitution rate of 90% or methacrylamide-modified carboxymethylcellulose with a graft substitution rate of 10%. And the macromolecule can also be other macromolecular, further, the graft substitution is optional and can be adjusted according to the actual situation.

Nitrobenzyl Light Trigger Modified Natural Biological Macromolecules

In some embodiments, the o-nitrobenzyl light trigger has a graft substitution rate of 1% to 100%. In some of the preferred embodiments, the o-nitrobenzyl light trigger modified natural biological macromolecules is represented by the formula (I), in the formula (I), R1 is —H, or is selected from ester bond, such as —CO(CH2)xCH3, —CO(CH2CH2O)xCH3, and —CO(CH2)x(CH2CH2O)yCH3; or ether bond, such as —(CH2)xCH3、—(CH2CH2O)xCH3、—(CH2)x(CH2CH2O)yCH3, or carbonate bond such as —COO(CH2)xCH3、—COO(CH2CH2O)xCH3, —COO(CH2)x(CH2CH2O)yCH3, or isocyanate bond, such as —CONH(CH2)xCH3、—CONH(CH2CH2O)xCH3, —CONH(CH2)x(CH2CH2O)yCH3, where x and y≥0 and are integers; R2 is —H, or is selected from —O(CH2CH2O)xCH3, —O(CH2)x(CH2CH2O)yCH3, where x and y≥0 and are integers; R3 is selected from amino-type linkages —O(CH2)xCONH(CH2)yNH—, halogenated linkage —O(CH2) x- and carboxyl linkage —O(CH2) xCO—, where x and y≥0 and are integers; R4 is —H or —CONH(CH2) xCH3, where x≥0 and is an integer; P1 stand for the biological macromolecule;

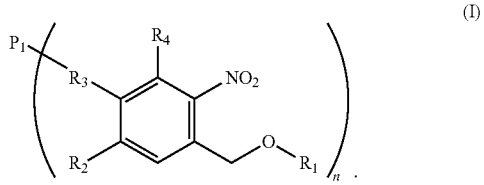

In some specific embodiments, the preferable o-nitrobenzyl type photo trigger is o-nitrobenzyl.

In some specific embodiments, the natural biological macromolecule in the natural biological macromolecule modified by o-nitrobenzyl light trigger is hyaluronic acid, gelatin, sodium alginate, chondroitin sulfate, silk fibroin, chitosan, Carboxymethyl cellulose or collagen in one or a mixture comprised by several kinds of them mentioned above.

Method

The present invention provides a method for rapidly hemostasis, which involves two steps. Covering the bleeding site with natural biological macromolecule which modified by light-responsive crosslinking group firstly and then illuminating. In some preferred embodiments, natural biological macromolecule modified by o-nitrobenzyl photo trigger is used to cover the bleeding site before illumination and then treated with light. In some other cases, natural biological macromolecules modified by light-responsive cross-linking groups and natural biological macromolecules modified by o-nitrobenzyl light trigger are mixed to form a mixture reagent firstly, and covering the bleeding site with the mixture, and then treated with light. In some preferred embodiments, the mixture also includes a photo initiator and/or deionized water. A preferred final mass concentration of the photo initiator is 0.001 to 1% based on the mass of deionized water. In some preferred embodiments, natural biological macromolecule modified by the photo-responsive cross-linking and natural biological macromolecule modified by the o-nitrobenzyl light trigger have a final mass concentration of 0.1 to 10% based on the mass of deionized water. Preferably, the photo-responsive crosslinking group in the photo-reactive crosslinking group-modified natural biological macromolecule has a graft substitution rate of 10 to 90%. Preferably, the light-responsive crosslinking group is methacrylamide or methacrylic anhydride. Preferably, the o-nitrobenzyl photo trigger in the o-nitrobenzyl photo trigger-modified natural biological macromolecule has a graft substitution rate of 1-100%.

In another aspect, the invention also provides a method for repairing biological tissue or hemostasis, which can be described as follows.

Providing a reagent contains natural biological macromolecule modified by photo-responsive cross-linking group, and applying the reagent to the injured biological tissue or bleeding tissue. The method includes injecting the light-control bio-glue onto a hemorrhagic wound or a tissue site that need to be repaired. In some preferred embodiments, the method comprises illuminating wound with light having a wavelength range of 350-450 nm and an energy density of 20-150 mW/cm$^2$. Preferably, the illumination time is 1 to 10 s. The biological glue can be cross-linked and solidified through above methods thus can be used to control bleed rapidly or repair the tissues. In some preferred embodiments, the reagent also includes natural biological macromolecule modified with o-nitrobenzyl type photo trigger. In some preferred embodiments, the reagent also includes a photo initiator and/or deionized water. A preferred final mass concentration of the photo initiator is 0.001 to 1% based on the mass of deionized water.

EXAMPLES

The present invention will be further described with specific embodiments. These descriptions merely show how the invention is implemented, but do not limit the scope of the present invention.

The preparation of natural biological macromolecule modified by o-nitrobenzyl type photo response is based on the method described in the following literature: Colosi C, Shin S R, Manoharan V, et al. Microfluidic Bioprinting of Heterogeneous 3D Tissue Constructs Using Low-Viscosity Bioink [J]. Advanced Materials, 2016, 28(4): 677-684). The whole content of the literature is one of the specific embodiments of the invention.

The preparation of O-nitrobenzyl type photo-trigger modified natural biological macromolecules is referred to the Chinese patent application 201410698239.0.

Example 1

150 mg o-nitrobenzyl-modified hyaluronic acid (HA-NB, synthesized according to Example 1 of the reference patent application 201410698239.0) with a graft substitution rate of 100%, 500 mg methacrylic acid Anhydride-modified gelatin (GELMA) with a graft substitution rate of 10% and 10 mg lithium phenyl (2,4,6-trimethylbenzoyl) phosphate (LAP) were dissolved in 10 mL (10 g) of deionized water. The light-control biological glue containing a mass concentration of 1.5% HA-NB, 5% GELMA and 0.1% LAP was formed after the solution was mixed thoroughly.

Applying the light-control biological glue prepared in step: 1) to the bleeding site of the wound, and then irradiating for 1 second with light having a wavelength band of 365 nm and an energy density of 60 mW/cm$^2$. Consequentially, the biological glue can solidify and achieve rapid hemostasis within 2 seconds.

Example 2

100 mg o-nitrobenzyl-modified sodium alginate (ALG-NB, synthesized according to the Example 2 of the reference patent application 201410698239.0) with a graft substitution rate of 50%, 200 mg methyl propylene with a graft substitution rate of 90% Amide-modified gelatin (GELMA) and 4 mg phenyl (2,4,6-trimethylbenzoyl) phosphate lithium salt (LAP) were dissolved in 10 mL of deionized water. The light-control biological glue containing a mass concentration of 1% ALG-NB, 2% GELMA and 0.04% LAP was formed after the solution was mixed thoroughly.

Applying the light-control biological glue prepared in step 1) to the bleeding site of the wound, and then irradiating for 2 second with light having a wavelength band of 350 nm and an energy density of 20 mW/cm². Consequentially, the biological glue can solidify and achieve rapid hemostasis within 5 seconds.

Example 3

300 mg o-nitrobenzyl-modified chondroitin sulfate (CS-NB, synthesized according to Example 1 of the reference patent application 201410698239.0) with a graft substitution rate of 10%, 10 mg Anhydride-modified gelatin (GELMA) with a graft substitution rate of 40% and 0.2 mg phenyl (2,4,6-trimethylbenzoyl) phosphate lithium salt (LAP) were dissolved in 10 mL of deionized water. The light-control biological glue containing a mass concentration of 3% CS-NB, 0.1% GELMA and 0.002% LAP was formed after the solution was mixed thoroughly.

Applying the light-control biological glue prepared in step 1) to the bleeding site of the wound, and then irradiating for 10 second with light having a wavelength band of 450 nm and an energy density of 150 mW/cm². Consequentially, the biological glue can solidify and achieve rapid hemostasis within 10 seconds.

Example 4

1 g o-nitrobenzyl modified gelatin (Gel-NB, synthesized according to the Example 1 of the reference patent application 201410698239.0) with a graft substitution rate of 30%, 1 g methyl methacrylate Amide-modified gelatin (GELMA) with a graft substitution rate of 20% and 20 mg phenyl (2,4,6-trimethylbenzoyl) lithium phosphate (LAP) were dissolved in 10 mL of deionized water. The light-control biological glue containing a mass concentration of 10% Gel-NB, 10% GELMA, and 0.2% LAP was formed after the solution was mixed thoroughly.

Applying the light-control biological glue prepared in step 1) to the bleeding site of the wound, and then irradiating for 2 second with light having a wavelength band of 385 nm and an energy density of 20 mW/cm². Consequentially, the biological glue can solidify and achieve rapid hemostasis within 2 seconds.

Example 5

10 mg o-nitrobenzyl modified silk fibroin (Silk-NB, synthesized according to Example 1 in reference patent application 201410698239.0) with a graft substitution rate of 90%, 600 mg methacrylic acid Anhydride-modified collagen (ColMA) with a graft substitution rate of 30% and 12 mg 2-hydroxy-4'-(2-hydroxyethoxy)-2-methylpropiophenone (12959) were dissolved in 10 mL of deionized water. The light-control biological glue containing a mass concentration of 0.1% Silk-NB, 6% MassMA, and 0.12% LAP was formed after the solution was mixed thoroughly.

Applying the light-control biological glue prepared in step 1) to the bleeding site of the wound, and then irradiating for 5 second with light having a wavelength band of 405 nm and an energy density of 100 mW/cm². Consequentially, the biological glue can solidify and achieve rapid hemostasis within 6 seconds.

Example 6

1) 500 mg o-nitrobenzyl modified collagen with graft substitution rate of 100% (Col-NB, synthesized according to Example 1 in reference patent application 201410698239.0) and 500 mg methacrylic anhydride modified sulfuric acid Chondroitin with graft substitution rate of 90% (SilkMA) and 10 mg 2-hydroxy-4'-(2-hydroxyethoxy)-2-methylpropiophenone (12959) were dissolved in 10 mL of deionized water to prepare a light-controlled biological gel solution containing HA-NB (5%, w/V), SilkMA (5%, w/V), and LAP (0.1%, w/V).

2) Applying the biological gel prepared in step 1) to the bleeding site of wound, and then irradiating for 5 s with light having a wavelength of 385 nm and energy density of 120 mW/cm². Consequentially, the biological gel can solidify and achieve rapid hemostasis within 5 seconds.

Example 7

500 mg o-nitrobenzyl modified chitosan with graft substitution rate of 10% (CS-NB, synthesized according to Example 3 in reference Chinese Patent Application No. 201410698239.0) and 500 mg methacrylic anhydride modified Carboxymethylcellulose with graft substitution rate of 10% (CMCMA) and 10 mg 2-hydroxy-4'-(2-hydroxyethoxy)-2-methylpropiophenone (12959) were dissolved in 10 mL of deionized water to prepare a light-controlled biological gel solution containing CS-NB (5%, w/V), CMCMA (5%, w/V), and LAP (0.1%, w/V).

Applying the biological gel prepared in step 1) to the bleeding site of wound, and then irradiating with light having a wavelength of 385 nm and energy density of 120 mW/cm² for 5 s. Consequentially, the biological gel can solidify and achieve rapid hemostasis within 5 seconds.

Example 8

1) 150 mg 0-nitrobenzyl modified hyaluronic acid with graft substitution rate of 5% (HA-NB, synthesized according to Example 1 in reference Chinese Patent Application No. 201410698239.0), 500 mg gelatin and 10 mg phenyl (2,4,6-trimethylbenzoyl) lithium phosphate (LAP) were dissolved in 10 mL of deionized water to prepare a light-controlled biological gel solution containing HA-NB (1.5%, w/V), gelatin (5%, w/V), and LAP (0.1%, w/V).

2) Applying the biological gel prepared in step 1) to the bleeding site of wound, and then irradiating with light having a wavelength of 365 nm and energy density of 60 mW/cm² for 30 s. This kind of biological glue solidified slowly, but it would be washed away by blood and unable to stop bleeding. It demonstrated that the application of o-nitrobenzyl modified macromolecular substance alone can't achieve rapid hemostasis, which further indicating that the light-responsive cross-linking groups modified natural biomacromolecules in our invention can significantly improve the hemostasis efficiency of light-triggering o-nitrobenzyl groups modified natural biological macromolecules.

Example 9

1) 100 mg gelatin and 10 mg phenyl (2,4,6-trimethylbenzoyl) lithium phosphate (LAP) were dissolved in 10 mL of deionized water to prepare a light-controlled biological gel solution containing gelatin (1.5%, w/V) and LAP (0.1%, w/V).

2) The biological gel prepared in step 1) was applied to the bleeding site of wound, and then irradiated with light having a wavelength of 365 nm and energy density of 60 mW/cm² for 60 s. This kind of biological glue solidified slowly, but it would be washed away by blood and unable to achieve hemostasis.

Example 10

The application of light-controlled biological gel to hemostasis and repair of rat hepatectomy.

Grouping and Reagents

The composition of light-controlled biological gel solution: 10% GelMA (grafting rate of 10%), 1.5% HA-NB (grafting rate of 7%), 0.05% LAP and deionized water.

The composition of light-controlled biological gel solution: 10% GelMA (grafting rate of 10%), 2.5% HA-NB (grafting rate of 10%), 0.1% LAP and deionized water.

The composition of light-controlled biological gel solution: 10% GelMA (grafting rate of 10%), 0.1% LAP and deionized water.

The composition of light-controlled biological gel solution: 10% Gelatin, 2.5% HA-NB (grafting rate of 10%), 0.1% LAP and deionized water.

Fibrin adhesive purchased from Shanghai Laise Blood Products Co., Ltd., batch number: Zhunzi 520030070.

Blank control: deionized water.

Experiments

The Sprague Dawley rats were used to receive a large hepatectomy as a trauma model. Comparatively, 6 materials (a: 5% GelMA, 1.5% HA-NB, 0.05% LAP, in-situ gelation; b: 10% GelMA, 2.5% HA-NA, 0.1% LAP, in-situ gelation; c: 10% GelMA, 0.1% LAP, in-situ gelation; d: 10% Gelatin, 2.5% HA-NA, 0.1% LAP, in-situ gelatin; e: commercial Fibrin adhesive; f: blank control group) were coated on the cut surface of hepatic lobe after hepatectomy to observe the results without other dispose. Each group contains 10 rats.

Observation was made after the application of the material (irradiating with light having a wavelength of 365 nm and energy density of 60 mW/cm² for 2 s after coating a, b, and c; irradiating with light having a wavelength of 365 nm and energy density of 60 mW/cm² for 2 s after coating group d; group e was coated directly; group f without any treatment). Bleeding in group a and b were immediately stopped after light-excitation, and then no bleeding was observed in 30 minutes; group c showed immediate gelation after illumination, but the adhesion was easy to fall off and blood continued to seep; group d showed slow gelation after illumination and bleed continued to seep, while gel washed away before it solidified completely, even if light was applied for more than 3 s; Fibrin in group e solidify at the cut surface quickly, but it easy to fall off and blood continued to leak; group f is bleeding.

Figure 2A:
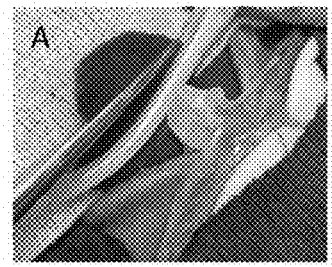
FIGS. 2A-2F show the process of hemostasis of a rat using light-control biological glue of the present invention after liver lobe was excised.
Figure 2B:
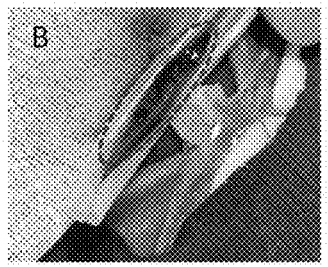
Figure 2C:
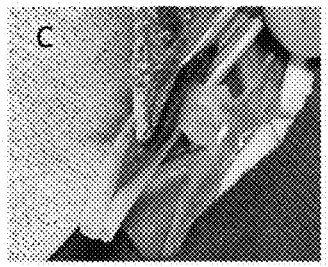
Figure 2F:
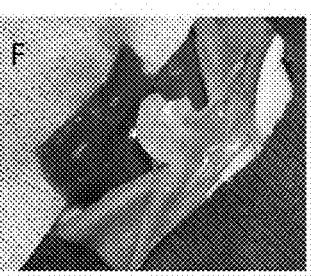
Figure 2E:
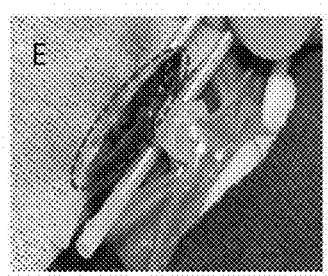
Figure 2D:
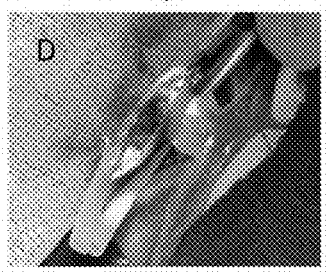

As shown in FIG. 2, the hemostasis situation of groups with light-controlled biological gel is obviously better than commercial Fibrin material and blank groups. These rats were postoperative suture and continue fed. It was observed that all rats in group E and F died after one week, one rat in group A was died, all rats in group B were survived, three rats in group C were died, and five rats in group D were died. 9 and 10 rats in group A and B survived, respectively, and were in good condition with increasing body weight after two weeks, proving that the light-controlled biological gel material of the present invention is bio-friendly to tissues and cells. In contrast, 5 and 2 rats in group c and d survived, respectively, but appeared to be wilt, thin and weak.

Example 11

The application of light-controlled biological gel to rabbit arterial defect hemostasis of (1) Grouping and reagents The composition of light-controlled biological gel solution: 5% GelMA (grafting rate of 20%), 1.5% HA-NB (grafting rate of 3%), 0.05% LAP and deionized water.

The composition of light-controlled biological gel solution: 10% GelMA (grafting rate of 10%), 0.1% LAP and deionized water.

The composition of light-controlled biological gel solution: 10% Gelatin, 2.5% HA-NB (grafting rate of 10%), 0.1% LAP and deionized water.

Fibrin adhesive purchased from Shanghai Laise Blood Products Co., Ltd., batch number: Zhunzi S20030070.

Blank control: deionized water.

Experiment

Figure 3A:
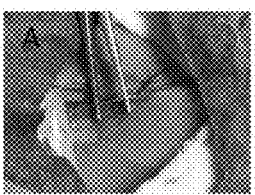
FIG. 3A-3H are photographs showing the process of rabbit femoral artery hemostasis by light-control biological glue of the present invention.
Figure 3B:
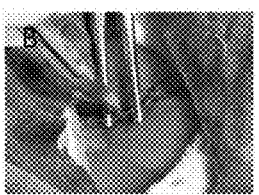
Figure 3C:
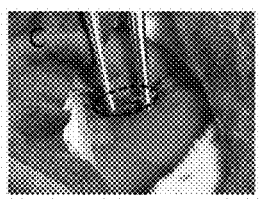
Figure 3D:
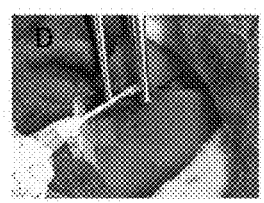
Figure 3H:
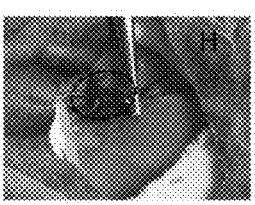
Figure 3G:
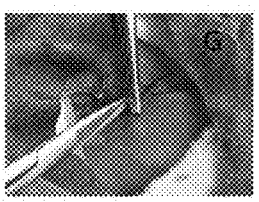
Figure 3F:
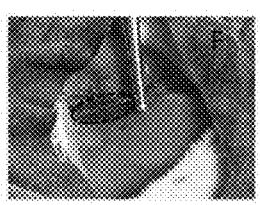
Figure 3E:
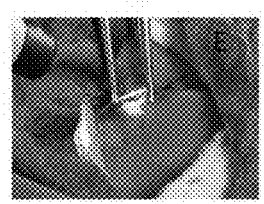

New Zealand male white rabbits were utilized as a trauma model and were divided into groups randomly according to weight before the experiment (five rabbits each group): a: 5% GelMA, 1.5% HA-NB, 0.05% LAP, in-situ gelation; b: 10% GelMA, 0.1% LAP in-situ gelation; c: 10% Gelatin, 2.5% HA-NA, 0.1% LAP in-situ gelation; d: commercial Fibrin adhesive, e: blank model group. Each animal received a femoral artery wound (1 mm large incision) to establish an arterial injury model. Applying the material (a-e) to the femoral artery injury (irradiating with light having a wavelength of 365 nm and energy density of 60 mW/cm² for 2 s after coating group a and b; irradiating with light having a wavelength of 365 nm and energy density of 60 mW/cm² for 30 s after coating group c; group d and e without irradiation), and then loosening the proximal end of the vascular clamp. As shown in FIG. 3, no bleeding was observed in group a in 30 minutes, proving that the light-controlled biological gel can stop bleeding at the artery injury. Furthermore, there was blood ejected when cut the distal end of the vessel, proving that the light-controlled biological gel did not block the artery. Group b showed immediate blood ejecting after loosening the proximal vascular clamp; in group c, the blood was ejected within 5 seconds after loosening the proximal vascular clamp, and followed by continued bleeding; in group d, the blood was ejected within 2 seconds after loosening the proximal vascular clamp, and followed by continued bleeding; in group e, the blood ejected immediately after loosening the proximal vascular clamp. These results demonstrated that the light-controlled biological gel has better hemostatic effects than commercial adhesives and control group.

Example 12

The application of light-controlled biological gel to rabbit intestinal leak repair.

Grouping and Reagents

The composition of light-controlled biological gel solution: 5% GelMA (grafting rate of 20%), 1.5% HA-NB (grafting rate of 7%), 0.05% LAP and deionized water.

Fibrin adhesive purchased from Shanghai Laise Blood Products Co., Ltd., batch number: Zhunzi S20030070.

Blank control: deionized water.

Experiment

New Zealand male white rabbits were utilized as a trauma model and were divided into groups randomly according to weight before the experiment (five rabbits each group): a:

5% GelMA, 1.5% HA-NB, 0.05% LAP, in-situ gelation; b: commercial Fibrin adhesive, c: blank model group. Each animal received a laparotomy and large intestine wound treatment (3 mm wound) to establish a model of intestinal leakage.

Figure 4A:
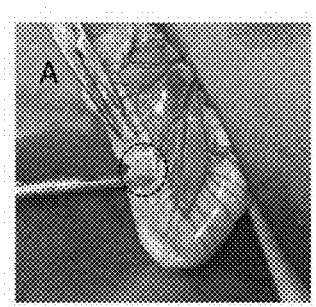
FIGS. 4A-4F show the process photographs by using light-control biological glue of the present invention for repairing of damaged rabbit large intestine.
Figure 4B:
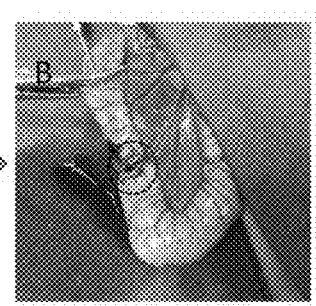
Figure 4C:
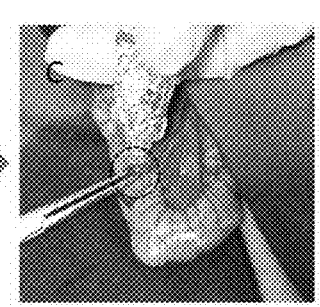
Figure 4F:
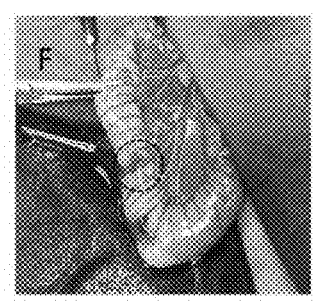
Figure 4E:
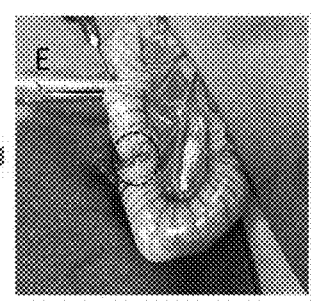
Figure 4D:
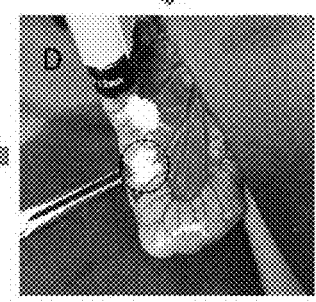

After applying the three materials to the wound (irradiating with light having a wavelength of 365 nm and energy density of 60 mW/cm$^2$ for 2 s after coating group a; group b was directly coated; group c without any treatment), iodophor was injected with syringe at the upper end of the intestine. As shown in FIG. 4, iodophor successfully pass the wound and intestinal swelled obviously without leakage in group a. After pierced at the lower end of the intestine, much iodophor leaked out, proving that the wound was blocked well without blocking internal intestinal tract. In group b, after injecting iodophor, the intestinal swelled obviously, followed by leakage of iodophor. In group c, iodophor directly leaked from wound without swelling. These results proved that light-controlled biological gel shows better wound bonding and block efficiency compared to commercial adhesive.

Example 13

1) 150 mg of o-nitrobenzyl modified hyaluronic acid (HA-NB, synthesized in Example 1 of Patent Application No. 201410698239.0) with a graft substitution ratio of 100%, 500 mg of methacrylic acid having a graft substitution ratio of 10% Anhydride-modified gelatin (GELMA), 10 mg of phenyl (2,4,6-trimethylbenzoyl) lithium phosphate (LAP) dissolved in 10 ml (ie 10 g) of deionized water and 10 mg of nano-amorphous phosphoric acid Calcium (Nano-ACP) is uniformly mixed in 10 ml deionized water and formulated into HA-NB with a mass concentration of 1.5%, GELMA with a mass concentration of 5%, LAP with a mass concentration of 0.1%, and NanoACP with a mass concentration of 0.1%.

2) The photo-controlled bio-glue prepared in the step 1) is irradiated with light having a wavelength of 365 nm and an energy density of 60 mW/cm$^2$ for 1 s to solidify the bio-gel, and then subjected to a biomineralization process. The mineralization process was recorded from 0 h, recorded at 24 h and 72 h, respectively, and observed by transmission electron microscopy, the mineralized crystals gradually increased (FIG. 5).

Example 14

1) 100 mg of o-nitrobenzyl modified sodium alginate (ALG-NB, synthesized in Example 2 of Patent Application No. 201410698239.0) having a graft substitution ratio of 50%, and 200 mg of methacryl having a graft substitution ratio of 90% Amide modified gelatin (GELMA), 4 mg of phenyl (2,4,6-trimethylbenzoyl) lithium phosphate (LAP) dissolved in 10 ml of deionized water and 4 mg of nano-tricalcium phosphate (NanoTCP) In 10 ml of deionized water, it was uniformly mixed and prepared into a light-controlled bio-glue containing ALG-NB with a mass concentration of 1%, GELMA with a mass concentration of 2%, LAP with a mass concentration of 0.04%, and NanoTCP with a mass concentration of 0.04%.

2) The photo-controlled bio-glue prepared in the step 1) is irradiated with light having a wavelength of 350 nm and an energy density of 20 mW/cm$^2$ for 2 s to solidify the bio-gel. And then subjected to a biomineralization process.

Example 15

1) 300 mg of o-nitrobenzyl modified chondroitin sulfate (CS-NB, synthesized in Example 1 of Patent Application No. 201410698239.0), 10 mg of methacrylic acid having a graft substitution ratio of 40% Anhydride-modified gelatin (GELMA), 0.2 mg of lithium phenyl (2,4,6-trimethylbenzoyl)phosphate (LAP) dissolved in 10 ml of deionized water and 5 mg of nano-hydroxyapatite (NanoHAP) In 10 ml of deionized water, it was uniformly mixed and formulated into a light-controlled bio-glue containing 3% by mass of CS-NB, a mass concentration of 0.1% GELMA, a mass concentration of 0.002% of LAP, and a mass concentration of 0.05% of NanoHAP.

2) The photo-controlled bio-glue prepared in the step 1) is irradiated with light having a wavelength of 450 nm and an energy density of 150 mW/cm$^2$ for 10 s to solidify the bio-gel, and then subjected to a biomineralization process.

Example 16

1) 1 g of o-nitrobenzyl modified gelatin having a graft substitution ratio of 30% (Gel-NB, synthesized in Example 1 of Patent Application No. 201410698239.0), 1 g of methacrylic acid having a graft substitution ratio of 20% Amide modified gelatin (GELMA), 20 mg of phenyl (2,4,6-trimethylbenzoyl) lithium phosphate (LAP) dissolved in 10 ml of deionized water and 7 mg of nano-tricalcium phosphate (NanoTCP) In 10 ml of deionized water, it was uniformly mixed and prepared into a light-controlled bio-glue containing 10% by mass of Gel-NB, 10% by mass of GELMA, 0.2% by mass of LAP and 0.07% by mass of NanoTCP.

2) The photo-controlled bio-glue prepared in the step 1) is irradiated with light having a wavelength of 385 nm and an energy density of 20 mW/cm$^2$ for 2 s to solidify the bio-gel, and then subjected to a biomineralization process.

Example 17

1) 10 mg of o-nitrobenzyl modified silk fibroin (Silk-NB, synthesized in Example 1 of Patent Application No. 201410698239.0), and 600 mg of methacrylic acid having a graft substitution ratio of 30% Anhydride-modified collagen (ColMA), 12 mg of 2-hydroxy-4'-(2-hydroxyethoxy)-2-methylpropiophenone (12959) dissolved in 10 ml of deionized water and 10 mg of nano-hydroxyphosphorus The stone (NanoHAP) was uniformly mixed in 10 ml of deionized water to prepare a light-controlled bio-glue containing 0.1% by mass of Silk-NB, 6% by mass of ColMA, 0.12% by mass of LAP and 0.1% by mass of NanoHAP.

2) The photo-controlled bio-glue prepared in the step 1) is irradiated with light having a wavelength of 405 nm and an energy density of 100 mW/cm$^2$ for 5 s to solidify the bio-gel, and then subjected to a biomineralization process.

Example 18

1) 500 mg of o-nitrobenzyl modified collagen (Col-NB, synthesized in Example 1 of Patent Application No. 201410698239.0), 500 mg of methacrylic anhydride modified with a graft substitution ratio of 90% Chondroitin sulfate (SilkMA), 10 mg of 2-hydroxy-4'-(2-hydroxyethoxy)-2-methylpropiophenone (12959) dissolved in 10 ml of deionized water and 8 mg of nano-amorphous calcium phosphate (NanoACP) was uniformly mixed in 10 ml of deionized water to prepare a light-controlled bio-glue containing 5% by mass of HA-NB, 5% by mass of SilkMA, 0.1% by mass of LAP, and 0.08% by weight of NanoACP.

2) The photo-controlled bio-glue prepared in the step 1) is irradiated with light having a wavelength of 385 nm and an energy density of 120 mW/cm² for 5 s to solidify the bio-gel, and then subjected to a biomineralization process.

Example 19

1) 500 mg of o-nitrobenzyl modified chitosan (CS-NB, synthesized in Example 3 of Patent Application No. 201410698239.0) with a graft substitution rate of 10%, and 500 mg of methacrylic acid having a graft substitution ratio of 10% Amide modified carboxymethyl cellulose (CMCMA), 10 mg of 2-hydroxy-4'-(2-hydroxyethoxy)-2-methylpropiophenone (12959) dissolved in 10 ml of deionized water and 9 mg of nano Tricalcium phosphate (NanoTCP) was mixed uniformly in 10 ml of deionized water to prepare light containing 5% mass concentration of CS-NB, mass concentration of 5% CMCMA, mass concentration of 0.1% LAP and mass concentration of 0.08% of NanoTCP. Control bio glue.

2) The photo-controlled bio-glue prepared in the step 1) is irradiated with light having a wavelength of 385 nm and an energy density of 120 mW/cm² for 5 s to solidify the bio-gel, and then subjected to a biomineralization process.

Example 20: Light-Controlled Bio-Glue Applied to the Repair of Rat Skull Defect (1) Grouping and Reagents:
A: light-controlled bio-glue plus nano-hydroxyapatite group: 5% GelMA (grafting rate 10%), 1.5% HA-NB (grafting rate 7%), 0.05% LAP, 0.1% nano-hydroxyphosphorus Stone, the solvent is deionized water; and the bio-glue obtained in Example 13-19 (without light treatment).
B: Light-controlled bio-glue group: 5% GelMA (graft ratio: 10%), 1.5% HA-NB (graft ratio: 7%), 0.05% LAP, solvent is deionized water.
C: Blank control: deionized water.

(2) Experiment
SD rats were used, and each rat received an 8 mm*8 mm square bone-removal operation of the skull parietal bone to establish a skull trauma model. In order to maintain data comparability, three sets of experimental materials were repeated three times:
A. light-controlled bio-glue plus nano-hydroxyapatite group and examples 13-19 (FIG. 6A);
B. Light control biological glue group (FIG. 6B);
C. blank control (FIG. 6C), After mixing A group of materials, the gel was irradiated with light with an energy density of 60 mW/cm² in the 365 nm band for 2 s, then cut into skull fragments of the skull defect size, and then the skull patch was placed in the skull defect of the rat.

B: After mixing the materials, the gel was irradiated with light with an energy density of 60 mW/cm² in the 365 nm band for 2 s, then cut into skull fragments of the skull defect size, and then the skull patch was placed in the skull defect of the rat, C. The blank group was not treated otherwise, and then the head skin was layered and sutured and continued to be raised.

5 rats are used in each group. After 5 weeks of application of the material, observe the experimental results.
The results are as follows:

| Experiments | thickness (mm) |
|---|---|
| A | 0.42 |
| B | 0.30 |
| C | 0.12 |
| Example 13 | 0.43 |
| Example 14 | 0.45 |
| Example 15 | 0.43 |
| Example 16 | 0.44 |
| Example 17 | 0.44 |
| Example 18 | 0.45 |
| Example 19 | 0.42 |

From the results above: In group A, among the skull fragments and each of the skull fragment around the place where 8 mm*8 mm square bone-removed can be mixed together (FIG. 6A) and the thickness of the bone is same as the normal; example 13-19 have the similar results. Comparing with A and B, the thickness of the bone is significantly higher than the group B.

In group B, among the skull fragments and each of the skull fragment around the place where 8 mm*8 mm square bone-removed can be mixed together but the thickness is lower than the normal (FIG. 6B).

In group C (FIG. 6C), almost no bone created.

The invention illustrated and described here can be practiced in the lack of any element or limitation that specifically disclosed to the invention. The terms and expressions employed are used as terms of description but not limitation, and it is not intended to exclude any equivalents of the features shown and describe in the use of these terms and expressions, and it should be recognized that each modification is possible within the scope of the present invention. It should be understood, therefore, that although the present invention has been specifically disclosed through various experiments and alternative features, modifications and variations of the concepts described herein can be adopted by one of ordinary skill in the art, and it is believed that such modifications and variations fall within the scope of the present invention and in the appended claims.

The contents of the articles, patents, patent applications, and all other documents and electronically available information described or documented herein are hereby incorporated by reference in their entireties to the same extent as if each individual publication was specifically separately pointed out for reference. Applicants reserve the right to incorporate any and all materials and information from any such articles, patents, patent applications or other documents in this application.

The present disclosure includes the following embodiments.

Paragraph 1A. An agent for homeostasis, wherein the agent includes a natural biological macromolecule modified by a photo-responsive cross-linking group.

Paragraph 2A. The agent according to paragraph 1A, wherein the reagent further includes a natural biological macromolecule modified with photo triggered o-nitrobenzyl groups.

Paragraph 3A. The agent of paragraph 1A, wherein the reagent further includes a photo initiator and/or deionized water.

Paragraph 4A. The agent of paragraph 1A, wherein the final concentration of the natural biological macromolecule modified by the light-responsive cross-linking group is 0.1 to 10% based on the mass of the deionized water.

Paragraph 5A. The reagent of paragraph 2A, wherein the final concentration of natural biological macromolecules modified by the photo triggered o-nitrobenzyl group is 0.1-10% based on the mass of the deionized water.

Paragraph 6A. The reagent of paragraph 3A, wherein the final mass concentration of the photo initiator is from 0.001 to 1% based on the mass of the deionized water.

Paragraph 7A. The reagent of paragraph 1A, wherein the light-responsive cross-linking group-modified natural biological macromolecule has a graft substitution rate of 10-90% of the photo-responsive cross-linking group.

Paragraph 8A. The reagent of paragraph 1A, wherein the photo-responsive cross-linking group is methacrylamide or methacrylic anhydride.

Paragraph 9A. The reagent of paragraph 2A, wherein the o-nitrobenzyl type photo initiator in the o-nitrobenzyl type photo initiator-modified natural bio-macromolecule has a graft substitution rate of 1-100%.

Paragraph 10A. The reagent of paragraph 1A, wherein the photo-reactive cross-linking group in the photo-reactive cross-linking group-modified natural biological macromolecule has a graft substitution rate of 5 to 90%.

Paragraph 11A. The reagent of paragraph 1A, wherein the light-responsive cross-linking group-modified natural bio-macromolecule is methacrylic anhydride-modified gelatin with a graft substitution rate of 10%, the graft substitution rate is 90% of methacrylamide-modified gelatin, methacrylic anhydride-modified gelatin with a graft substitution of 40%, methacrylamide-modified gelatin with a substitution of 20%, gelatin with a graft substitution of 30% methacrylic anhydride-modified collagen, methacrylic anhydride-modified chondroitin sulfate with a graft substitution rate of 90%, or methacrylamide-modified carboxymethylcellulose with a graft substitution rate of 10%.

Paragraph 12A. The reagent of paragraph 2A, wherein the o-nitrobenzyl type photo initiator modified natural biological macromolecule is o-nitrobenzyl modified hyaluronic acid with graft substitution rate of 100% O-nitrobenzyl-modified sodium alginate with a substitution rate of 50%, o-nitrobenzyl modified chondroitin sulfate with a substitution rate of 10%, o-nitrobenzyl with a substitution rate of 30% Modified gelatin, o-nitrobenzyl modified silk fibroin with graft substitution rate of 90%, o-nitrobenzyl modified collagen with graft substitution rate of 100% or o-nitro group with 10% graft substitution benzyl-modified chitosan.

Paragraph 13A. The reagent according to paragraph 2A, wherein the natural biological macromolecule in the natural biological macromolecule is hyaluronic acid, gelatin, sodium alginate, chondroitin sulfate, silk fibroin, chitosan Sugar, carboxymethyl cellulose or collagen, or a mixture comprised by several kinds of them.

Paragraph 14A. The reagent according to paragraph 3A, wherein the photo initiator is 2-hydroxy-4'-(2-hydroxyethoxy)-2-methylpropiophenone or phenyl 6-trimethylbenzoyl) phosphate lithium salt.

Paragraph 15A. A method of repairing a tissue lesion or homeostasis in a living organism comprising: providing an agent comprising a native biological macromolecule modified by a photo-responsive cross-linking group; contacting the agent to a bleeding site, and then irradiating the agent.

Paragraph 16A. The method according to paragraph 15A, wherein the irradiation is a light irradiation with a wavelength band of 350 to 450 nm and an energy density of 20 to 150 mW/cm$^2$.

Paragraph 17A. The method according to paragraph 16A, wherein the irradiation time is 1 to 10 s.

Paragraph 18A. The method according to paragraph 15A, wherein the reagent further includes a natural biological macromolecule modified with an o-nitrobenzyl type photo trigger.

Paragraph 19A. The method of paragraph 15A, wherein the reagent further includes a photo initiator and/or deionized water.

Paragraph 20A. The method of paragraph 15A, wherein the light-responsive cross-linked group-modified native biological macromolecule final concentration is 0.1-10% based on the mass of the deionized water.

Paragraph 21A. The method of paragraph 18A, wherein the o-nitrobenzyl type photo trigger is modified to have a final native biological macromolecule concentration of 0.1% to 10% based on the mass of the deionized water.

Paragraph 22A. The method of paragraph 19A, wherein the photo initiator mass final concentration is 0.001-1% based on the mass of deionized water.

Paragraph 23A. The method of paragraph 15A, wherein the light-responsive cross-linking group-modified natural biological macromolecule has a graft substitution rate of 10-90% of the photo-responsive cross-linking group.

Paragraph 24A. The method of paragraph 15A, wherein the light responsive cross-linking group is methacrylamide or methacrylic anhydride.

Paragraph 25A. The method of paragraph 18A, wherein the o-nitrobenzyl type photo initiator of the o-nitrobenzyl type photo initiator-modified natural bio-macromolecule has a graft substitution rate of 1-100%.

Paragraph 26A. The method according to paragraph 15A, wherein the photo-reactive cross-linking group in the photo-responsive cross-linking group modified natural biopolymer has a graft substitution rate of 5-90%.

Paragraph 27A. The method according to paragraph 15A, wherein said photo-responsive cross-linked group-modified native biological macromolecule is methacrylic anhydride-modified gelatin with a graft substitution rate of 10%, a graft substitution rate of 90% Methacrylamide-modified gelatin, methacrylic anhydride-modified gelatin with a graft substitution of 40%, methacrylamide-modified gelatin with a graft substitution of 20%, methyl with a graft substitution of 30% Acrylic anhydride-modified collagen, methacrylic anhydride-modified chondroitin sulfate with a graft substitution rate of 90%, or methacrylamide-modified carboxymethyl cellulose with a graft substitution rate of 10%, or a mixture comprised by several kinds of them.

Paragraph 28A. The method according to paragraph 18A, wherein the o-nitrobenzyl type photo-triggered natural biopolymer is o-nitrobenzyl-modified hyaluronic acid with a graft substitution rate of 100% O-nitrobenzyl-modified sodium alginate at a rate of 50%, o-nitrobenzyl-modified chondroitin sulfate at a graft substitution rate of 10%, o-nitrobenzyl modified at a graft substitution rate of 30% Gelatin, o-nitrobenzyl-modified silk fibroin with 90% graft substitution rate, o-nitrobenzyl-modified collagen with 100% graft substitution or o-nitrobenzyl group with 10% graft substitution Modified chitosan, or a mixture comprised by several kinds of them.

Paragraph 29A. The method according to any one of paragraphs 15A-28A, wherein the native biological macromolecules in the native biological macromolecules are hyaluronic acid, gelatin, sodium alginate, chondroitin sulfate, silk fibroin, chitosan, Carboxymethyl cellulose or collagen, or a mixture comprised by several kinds of them.

Paragraph 30A. The method according to paragraph 19A, wherein said photo initiator is 2-hydroxy-4'-(2-hydroxyethoxy)-2-methylpropiophenone or phenyl Methylbenzoyl) phosphate lithium salt.

We claim:

1. A reagent for repairing biological damage or homeostasis, wherein the agent comprises: a natural biological macromolecule modified with a light-responsive cross-linking group; a natural biological macromolecule modified with an o-nitrobenzyl type light initiator; a light initiator; and deionized water.

2. The reagent of claim 1, wherein the final concentration of the natural biological macromolecule modified with the light-responsive cross-linking group is 0.1 to 10% based on the mass of the deionized water.

3. The reagent of claim 2, wherein the final concentration of the natural biological macromolecule modified with the o-nitrobenzyl type light initiator is 0.1-10% based on the mass of the deionized water.

4. The reagent of claim 3, wherein the final mass concentration of the light initiator is from 0.001 to 1% based on the mass of the deionized water.

5. The reagent of claim 3, wherein the o-nitrobenzyl type light initiator in the o-nitrobenzyl type light initiator-modified natural biological macromolecule has a graft substitution rate of 1-100%.

6. The reagent of claim 3, wherein the o-nitrobenzyl type light initiator modified natural biological macromolecule is o-nitrobenzyl modified hyaluronic acid with a graft substitution rate of 100%, o-nitrobenzyl-modified sodium alginate with a graft substitution rate of 50%, o-nitrobenzyl modified chondroitin sulfate with a graft substitution rate of 10%, o-nitrobenzyl with a graft substitution rate of 30%, modified gelatin, o-nitrobenzyl modified silk fibroin with a graft substitution rate of 90%, o-nitrobenzyl modified collagen with a graft substitution rate of 100%, o-nitrobenzyl-modified chitosan with a graft substitution rate of 10%, or combinations thereof.

7. The reagent of claim 2, wherein the light-responsive cross-linking group-modified natural biological macromolecule has a graft substitution rate of 10-90% of the light-responsive cross-linking group.

8. The reagent of claim 2, wherein the light-responsive crosslinking group is methacrylamide or methacrylic anhydride.

9. The reagent of claim 2, wherein the light-responsive cross-linking group in the light-responsive cross-linking group-modified natural biological macromolecule has a graft substitution rate of 5 to 90%.

10. The reagent of claim 2, wherein the light-responsive cross-linking group-modified natural biological macromolecule is methacrylic anhydride-modified gelatin with a graft substitution rate of 10%, methacrylamide-modified gelatin with a graft substitution rate of 90%, methacrylic anhydride-modified gelatin with a graft substitution rate of 40%, methacrylamide-modified gelatin with a graft substitution rate of 20%, gelatin with a graft substitution rate of 30%, methacrylic anhydride-modified collagen, methacrylic anhydride-modified chondroitin sulfate with a graft substitution rate of 90%, methacrylamide-modified carboxymethylcellulose with a graft substitution rate of 10%, or combinations thereof.

11. The reagent of claim 1, wherein the natural biological macromolecule modified with the light-responsive cross-linking group is hyaluronic acid, gelatin, sodium alginate, chondroitin sulfate, silk fibroin, chitosan sugar, carboxymethyl cellulose or collagen.

12. The reagent of claim 11, wherein the light initiator is 2-hydroxy-4'-(2-hydroxyethoxy)-2-methylpropiophenone or phenyl 6-trimethylbenzoyl phosphate lithium salt.

13. The reagent of claim 1, wherein the natural biological macromolecule modified with the o-nitrobenzyl type light initiator is hyaluronic acid, gelatin, sodium alginate, chondroitin sulfate, silk fibroin, chitosan sugar, carboxymethyl cellulose or collagen.

* * * * *